United States Patent [19]

Lejdeborn et al.

[11] Patent Number: 5,147,293
[45] Date of Patent: Sep. 15, 1992

[54] APPARATUS FOR LIQUID FLUSHING OF BODY CAVITIES AND/OR SUPPLYING ACTIVE SUBSTANCE TO SUCH CAVITIES

[76] Inventors: Lars Lejdeborn, Västergöksvägen 70, Vällingby, Sweden, S-162 24; Olle Berg, Elfviksvägen 66, Lidingö, Sweden

[21] Appl. No.: 573,169
[22] PCT Filed: Mar. 17, 1989
[86] PCT No.: PCT/SE89/00146
  § 371 Date: Nov. 5, 1990
  § 102(e) Date: Nov. 5, 1990
[87] PCT Pub. No.: WO89/08470
  PCT Pub. Date: Sep. 21, 1989

[30] Foreign Application Priority Data
  Mar. 18, 1988 [SE] Sweden ............ 8801003

[51] Int. Cl.[5] ............ A61M 1/00; A61M 5/315
[52] U.S. Cl. ............ 604/38
[58] Field of Search ............ 604/36, 37, 38, 104

[56] References Cited

U.S. PATENT DOCUMENTS

| | | | |
|---|---|---|---|
| 756,252 | 4/1904 | Locke | 604/104 X |
| 930,312 | 8/1909 | Neveu | 604/38 |
| 973,456 | 10/1910 | Neveu | 604/38 |
| 1,115,107 | 10/1914 | Rice | 604/38 |
| 4,709,705 | 12/1987 | Truglio | 604/38 X |

*Primary Examiner*—William H. Grieb
*Attorney, Agent, or Firm*—Fleit, Jacobson, Cohn, Price, Holman & Stern

[57] ABSTRACT

Apparatus (2) for liquid flushing of body cavities and/or supplying an active substance to the body cavities includes a piston/cylinder device (3), a device (9,10) for manual actuation of the piston (8) and a nozzle (4) projecting from the piston/cylinder device (3) adapted for insertion of the free end (12) of the nozzle in the body cavity. The nozzle (4) is formed with two separated channels (5,6) each terminating at an outer end in a free end of the nozzle, one of the channels (6) extending in the wall of the cylinder (7) and an inner end terminating at the end of the cylinder immersed in the liquid (b) in a receptacle (1) containing the liquid and connected to the piston/cylinder device, the other channel (5) having an inner end communicating with a space (A) above the liquid in the container (1) and a piston rod (9) having a return spring (11). Upon reciprocating movement of the piston (8) in the cylinder (7), with the open end of the cylinder (7) immersed in the liquid (B), air in the channels (5,6) and at least an essential amount of the air in the body cavity is initially flushed by liquid flowing into channel (6) from the inner end thereof into space (a).

20 Claims, 1 Drawing Sheet

APPARATUS FOR LIQUID FLUSHING OF BODY CAVITIES AND/OR SUPPLYING ACTIVE SUBSTANCE TO SUCH CAVITIES

BACKGROUND OF THE INVENTION

The present invention relates to an apparatus for liquid flushing of body cavities and/or supply of active substance, for instance medicine, to such cavities. Such body cavities can be ears, vagina, wounds, bronchial tree, intestines, etc. Besides cleaning body cavities, the apparatus can be used for sample examinations, wherein for example cells (cancer tests) or infected materials (bacteria, fungeus, virus such as AIDS, etc.) are rinsed out and analyzed.

Ear wax plugs and inconveniencies connected therewith are a great problem. Every fifteenth visit in a ENT department is estimated to be caused by unsatisfying cleaning of ears. Such patients are also often taken care of by consultants and in non-hospital offices.

ENT-specialists usually remove wax plugs by high pressure flushing and/or by suction or by manual cleaning. These methods are reliable, however they are time consuming and personally demanding. High pressure flushing is the most effective method at present. Owing to the risk for tympanic membrane perforation and injure to the ear canal the method cannot be recommended for ones own use, nor for unskilled staff.

In non-hospital offices the patients either receive a recommendation to use a product for ones own use which is at present existing in the market, which however does not in a satisfactory way solve the problems for most patients, or attempts are made to flush the ears unless a consultation request is given to an ENT specialist.

As to other fields for use of an apparatus according to the invention, diagnostic search and treatment of lung disorders is at present usually carried out in such a way that first the patient is anaesthetized, possibly locally anaesthetized, however usually not in an AIDS search, whereupon a fiber instrument, so called bronchoscope, is moved down into the lung. The bronchoscope is provided with a channel through which a plastic hose is moved down to a small segment in the lung. Liquid is thereafter flushed through the hose and most of the liquid is later sucked back by an ordinary injection syringe. From the syringe the liquid is transmitted to various different sample vessels.

This search method has several disadvantages, among other things it is time-consuming owing to the general anesthesia which usually is required. The bronchoscope is a comparatively large instrument moved down through the respiratory tract. Moreover, a certain risk for infections exists during the different steps in such a method. It can finally be mentioned that patients in most cases must remain in the hospital.

BRIEF SUMMARY OF THE INVENTION

The present invention has been developed in order to eliminate the above-mentioned disadvantages and in a simple and reliable way carry out liquid flushing for cleaning and/or sampling and/or supplying an active substance.

The apparatus according to the invention includes a piston/cylinder-device, means for manual activation of the piston, and an insertion tube or hose projecting from the piston/cylinder-device adapted for insertion of the free end of the tube or hose into the body cavity and provided with two separated channels terminating in the free end of the insertion tube or hose and at opposite sides of the piston, wherein, after the application of the insertion tube or hose, a closed flush system for reciprocating flow of the liquid upon the movement of the piston between its end positions in the cylinder is formed.

Constructively, such an apparatus for flushing vagina is disclosed for example in U.S. Pat. Nos. 973,456 and 1,115,107. The construction according to the last-mentioned patent is an improvement of the construction according to the first-mentioned patent, which is mentioned to have the disadvantage that only a part of the liquid returns to the cylinder chamber during the movements of the piston, while the greater part of the liquid being prevented from entering the chamber by the presence of air remaining in the vagina. This disadvantage is eliminated by providing passages between channels or ducts in the nozzle tube.

Published application PCT/FR87/00131 discloses a device for washing ears. This device includes one chamber containing the liquid to be instilled and another chamber containing the used instilled liquid. The liquid is only injected once in one direction. Thus, the device is built such that recirculation shall be avoided, and it is expressively mentioned in the application that the invention rejects constructions operating with reciprocating flushing.

As distinguished from the above-mentioned known constructions, the apparatus according to the present invention is characterized in that it furthermore includes a closed receptacle for the liquid, that the cylinder and the channel terminating on the side of the piston facing the recepticle are immersed in the liquid in the receptacle, and that laterally of the cylinder above the liquid level in the receptacle there is a space for collecting during the first piston stroke or strokes the air existing in the flush system at the start of the flushing and at least an essential part of the air existing in the body cavity.

The invention hereby provides an apparatus having a closed flush system, which apparatus owing to its construction, besides providing an effective and simple cleaning and/or medicination of the body cavity and/or sampling, also avoids pressure increase in the cavity, whereby risks for injures in the cavity are eliminated, for example risks for tympanic membrane perforation and ear canal injury when used for liquid flushing of ears. The positive pressure created in one of the channels corresponds to the negative pressure by suction action created in the other channel. In other words, the volume pressed into one of the channels is equal to the volume sucked out of the other channel. Owing to evacuation of air, which takes place at least mainly during the first piston stroke, upon treatment of ears the discomfort is eliminated which otherwise occurs when air/liquid is flowing through the ear causing unpleasant buzzing for the patient. These advantages along with the simplicity in the construction and handling imply that the apparatus according to the invention is, particularly for ears, well adapted for self-care and can be handled by unskilled personal. Also upon the treatment of other body cavities than ears it is an advantage that air is evacuated. Otherwise a frothing wash liquid or sampling liquid can be obtained, the re-suction of which can be obstructed by the froth. Moreover, it is in certain cases, for example some wounds such as abdominal injuries, an advantage when existing air is decreased, viz. when it is desirable that the cavity shall decrease in volume, i.e. contract.

When treating lungs several advantages are obtained by the present invention compared with the above described known treatment methods. Instead of using a bronchoscope only a considerably narrower hose is inserted through the respiratory tract, which also means that only local anaesthesia of the upper respiratory tract and trachea is needed. Sampling can therefore be carried out in a policlinic, i.e. the patient does not need to stay in the hospital. Another and very essential advantage obtained by using an apparatus according to the invention is the hygienic handling of the sample liquid, which is collected in the receptacle without infection risk for personal (for instance in AIDS-diagnostics) and the entire receptacle can be sent for analysis. Moreover, the risk that infection is transferred to another patient is eliminated, which is an important aspect particularly concerning AIDS- and tuberculosis diagnostic.

BRIEF DESCRIPTION OF THE DRAWINGS

The invention is with reference to the accompanying drawing described more in detail in an embodiment particularly intended for ear treatment, wherein.

DETAILED DESCRIPTION

Figure 1:
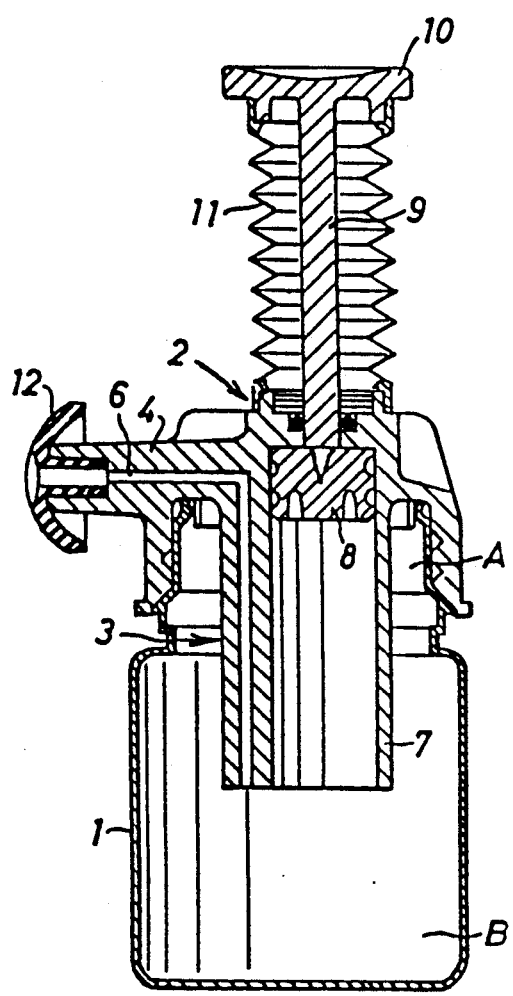
FIG. 1 shows a section along the line I—I in FIG. 2.
Figure 2:
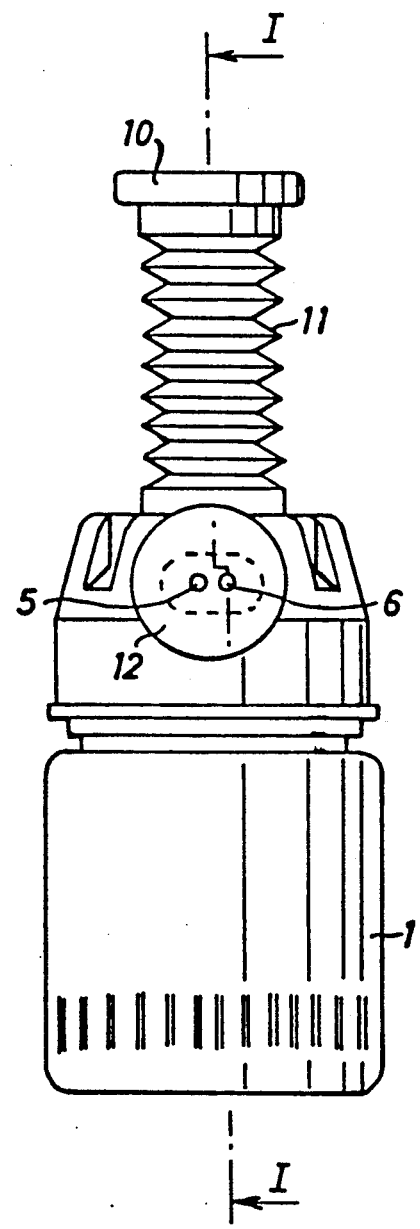
FIG. 2 shows a side view seen from the left in FIG. 1.

The apparatus illustrated in the drawing comprises in its principle parts a receptacle 1 for the liquid to be flushed and a unit, generally designated with the reference numeral 2, consisting of a piston/cylinder-device, generally designated with the reference numeral 3, and a nozzle or insertion tube 4 projecting from the piston/cylinder-device. The receptacle 1 is in an appropriate way detachably fastened to the unit 2, for instance by a screw connection, and forms a closed space after assembling these parts.

The insertion tube is formed with two channels 5 and 6. One channel, channel 5, is connected to the upper part of the cylinder 7, while the other channel, channel 6, in the shown embodiment extends through the cylinder wall and terminates at the same level with the open end of the cylinder 7. One end of a piston rod 9 is connected to the piston 8 in the piston/cylinder-device 3 and the opposite end of the piston rod is formed as a press button 10 for manual actuation. Spring means 11 surrounding the piston rod 9 is positioned between the press button 10 and the unit 2. Finally, the apparatus has sealing means 12 adapted to the ear and made by soft elastic material.

When using the apparatus the cylinder 7 and the channel 6 are immersed in liquid B in the receptacle 1 and above the liquid there is an air space A. Hereby, a closed flush system has together with the ear been formed for reciprocating flow of the liquid upon the movement of the piston 8 between its end positions in the cylinder 7. During the first piston stroke, or strokes inwardly toward receptacle 1 the air existing in the flush system and the ear canal will be evacuated therefrom and be collected in the air space A in the receptacle, whereupon there is only liquid in the flush system.

When using the apparatus in other connections than ear treatment mentioned above, the insertion tube 4 can have another length adapted to the connection in question and the sealing means 12 can be formed for adaption to the application and the body cavity being treated. Instead of a stiff insertion tube 4 as shown on the drawing a hose can be connected to the apparatus, for example to the insertion tube or to another connection means.

As shown in FIG. 1 the sealing means 12 is detachably inserted in the free end of the insertion tube 4. Different types and sizes of the sealing means 12 can be arranged for adaptation to the size and form of the body cavity being treated.

The invention is not limited to the embodiment described above and shown on the drawing but can be varied in several ways within the framework of the following claims.

We claim:

1. In an apparatus for liquid flushing of body cavities and/or supplying an active substance to such cavities, for example, medicines, including a piston/cylinder-device, means for manual activation of the piston, and an insertion tube projecting from the piston/cylinder-device having a free end adapted for insertion into the body cavity and having two separated channels each terminating at one outer end in said free end of the insertion tube of the piston, the insertion of the insertion tube into the body cavity producing a closed flush system for reciprocating flow of liquid upon reciprocating movement of the piston between end positions thereof in the cylinder, the improvement comprising:
    a closed receptacle connected to said piston/cylinder device for containing said liquid, one side of the piston facing said receptacle;
    an open end on said cylinder on said side of said piston facing said receptacle and immersed in said liquid in said receptacle;
    an inner end on one of said channels immersed in said liquid in said receptacle;
    a space in said receptacle above the level of said liquid therein; and
    an inner end on the other of said channels communicating with said space, so that air in said channels and at least an essential part of the air in the body cavity is driven into said space through said other of said channels by reciprocation of said piston in said cylinder.

2. The apparatus as claimed in claim 1, and further comprising:
    means for detachably connecting said receptacle to said piston/cylinder device.

3. The apparatus as claimed in claim 2 wherein:
    said insertion tube and said piston/cylinder device comprise an integral unit.

4. The apparatus as claimed in claim 3 wherein:
    said one of said channels extends in a wall of said cylinder.

5. The apparatus as claimed in claim 4 wherein:
    said inner end on said one of said channels is proximate said open end of said cylinder.

6. The apparatus as claimed in claim 5 wherein:
    said means for manual activation of said piston comprises spring loaded piston rod means.

7. The apparatus as claimed in claim 4 wherein:
    said means for manual activation of said piston comprises spring loaded piston rod means.

8. The apparatus as claimed in claim 3 wherein:
    said means for manual activation of said piston comprises spring loaded piston rod means.

9. The apparatus as claimed in claim 2 wherein:

said one of said channels extends in a wall of said cylinder.

10. The apparatus as claimed in claim 9 wherein:
said inner end on said one of said channels is proximate said open end of said cylinder.

11. The apparatus as claimed in claim 2 wherein:
said means for manual activation of said piston comprises spring loaded piston rod means.

12. The apparatus as claimed in claim 1 wherein:
said insertion tube and said piston/cylinder device comprise an integral unit.

13. The apparatus as claimed in claim 12 wherein:
said one of said channels extends in a wall of said cylinder.

14. The apparatus as claimed in claim 13 wherein:
said inner end on said one of said channels is proximate said open end of said cylinder.

15. The apparatus as claimed in claim 12 wherein:
said means for manual activation of said piston comprises spring loaded piston rod means.

16. The apparatus as claimed in claim 1 wherein:
said one of said channels extends in a wall of said cylinder.

17. The apparatus as claimed in claim 16 wherein:
said inner end on said one of said channels is proximate said open end of said cylinder.

18. The apparatus as claimed in claim 17 wherein:
said means for manual activation of said piston comprises spring loaded piston rod means.

19. The apparatus as claimed in claim 16 wherein:
said means for manual activation of said piston comprises spring loaded piston rod means.

20. The apparatus as claimed in claim 1 wherein:
said means for manual activation of said piston comprises spring loaded piston rod means.

* * * * *